United States Patent [19]

Marinkovich et al.

[11] 4,190,774
[45] Feb. 26, 1980

[54] RADIOGRAPHIC TABLE SYSTEM

[75] Inventors: Cedomir S. Marinkovich, Chicago; William M. Crimmins, Vernon Hills, both of Ill.

[73] Assignee: Litton Industrial Products Inc., Beverly Hills, Calif.

[21] Appl. No.: 884,906

[22] Filed: Mar. 9, 1978

[51] Int. Cl.² ............................................. A61B 6/04
[52] U.S. Cl. .................................... 250/446; 250/447
[58] Field of Search ............................... 250/446, 447

[56] References Cited

U.S. PATENT DOCUMENTS

2,208,258   7/1940   Grobe .............................. 250/446

Primary Examiner—Alfred E. Smith
Assistant Examiner—T. N. Grigsby
Attorney, Agent, or Firm—Robert A. Seldon

[57] ABSTRACT

A radiographic fluoroscopic X-ray table including a rigid fluoroscopic staging apparatus where the spot film device is synchronized along the transverse axis with the X-ray tube by means of a telescoping shaft assembly. The telescoping shaft assembly engages a rack in the spot film device and drives a sprocket and chain system connected to the X-ray tube and collimator. The telescoping shaft also increases and decreases its length to accomodate the spot film device being moved up and down in the vertical direction above the table. The spot film device and the fluoroscopic staging aparatus are counterbalanced in the vertical direction and along the table's longitudinal axis through a system of pulleys, cables and counterweights. A power assist system is provided to drive the staging apparatus along the longitudinal axis of the X-ray table.

14 Claims, 10 Drawing Figures

Fig_1

Fig_10

Fig_2

Fig_3

Fig_5

Fig_6

Fig_7

Fig_8

Fig_9

RADIOGRAPHIC TABLE SYSTEM

FIELD OF THE INVENTION

This invention relates to the field of radiographic fluoroscopic X-ray tables as generally used in the field of medicine.

BACKGROUND OF THE INVENTION

A radiographic fluoroscopic X-ray table is one capable of being used for radiographic X-ray procedures and for fluoroscopic X-ray procedures. In a typical radiographic procedure, X-ray film is positioned in the table body below the tabletop in alignment with an X-ray tube suspended over the table and generally supported by a roller track attached to the ceiling or other means independent from the table itself. The X-ray tube and the film are positioned such that a patient lying on the table will have that portion of his body to be X-rayed located in the path of the X-ray beams directed from the tube towards the film.

The radiographic fluoroscopic table has the additional feature of an X-ray tube located in the table body beneath the table's top and a spot film device attached to the table and located over the surface. The spot film device contains a film cassette which records the X-ray image of the patient produced by the X-ray tube located in the table. The technician has the option of removing the film cassette from the path of the X-ray beams and permitting the beams to pass through an image intensifier mounted on the spot film device. After passing through the image intensifier, the beams are coupled into an optical distributor which can distribute the image among any of three cameras also mounted on the spot film device; a television camera which is connected to a monitor located in the X-ray room a spot film camera which contains 105 millimeter X-ray film and is capable of taking up to 12 frames per second, and a 35 millimeter cine camera which takes up to 70 frames per second of the X-ray image being transferred through the image intensifier and optical distributor.

The television camera is useful because it allows the technician for the X-ray table to monitor the X-ray images and select the right portion of the body or the right instant at which an X-ray should be taken. The spot film camera adds the additional option of being able to monitor using a television camera while taking X-ray pictures. While the film in the spot film camera is smaller than that contained in the film cassette, it is still sufficiently large to give adequate resolution for most X-ray analysis.

The 35 mm cine camera adds the additional option of being able to record dynamic events on X-ray film. However, due to the fact that the film is much smaller, resolution is greatly decreased and the quality of the picture is much lower than X-ray pictures taken using a film cassette or a spot film camera. The 35 mm cine camera is generally used only for specialized procedures such as heart studies. A spot film device which includes all of the above three cameras is called a three port system. Spot film devices are also produced which include only one or two of the three camera options and are known respectively as one port and two port systems.

The spot film device is supported over the table by a fluoroscopic staging structure. This staging structure has heretofore included a carriage system located underneath the table's upper surface, comprising a longitudinal carriage and a transverse carriage which respectively allows the spot film device to travel the length and width of the X-ray table. The X-ray tube in the table is attached to the carriage structure such that it is always located directly below the spot film device and aimed at the image intensifier mounted thereon.

The fluoroscopic staging apparatus also includes a vertical carriage which allows the spot film device to be lowered or raised with respect to the table surface. This vertical carriage is counterbalanced using cables and pulleys with weights located in the table itself so as to allow the spot film device to be raised and lowered manually with minimum effort. In addition, the entire fluoroscopic staging apparatus, including carriages and spot film device, must be counterbalanced along the longitudinal axis of the table, because the table, of which it is part, tilts with respect to the horizontal along its longitudinal axis. For the sake of clarity, the term "vertical", as used herein, with respect to the radiographic system shall mean vertical with respect to the table surface to allow for X-ray tables which may tilt.

The problem in the past has been to adequately support a three port spot film device on an X-ray table with a transverse carriage and a longitudinal carriage. The transverse carriage is conventionally attached to the longitudinal carriage by a system of roller bearings and track in the longitudinal carriage. The longitudinal carriage in turn is attached to the table by means of a bearing and track system which permits movement in the longitudinal direction with respect to the table. With a three port spot film device, the use of both a transverse carriage and a longitudinal carriage has resulted in impermissable deflection in the staging structure. Using both of these carriages in the table, each carriage having its own roller and track system, there has been insufficient rigidity in the staging apparatus due to movement or "give" in the track assemblies. Under the load, carried by the carriage system, which is usually over 400 pounds, the fluoroscopic staging apparatus deflects beyond permissible ranges. The problem is particularly acute when the table is of the type which can tilt ± 90° from horizontal. To overcome this problem, an overhead suspension system supported by the ceiling above the table has heretofore been employed to partially support the weight of a three port spot film device, thereby decreasing deflection. In addition to the resulting awkward installation of the table within the room, however, the longitudinal and transverse movement of the staging requires the movement of a substantial mass of material in the transverse longitudinal carriages requiring, in turn, substantial effort on the part of the technician.

SUMMARY OF THE INVENTION

An important aspect of this invention is to provide a rigid fluoroscopic staging apparatus capable of independently supporting up to and including a three port spot film system above a radiographic fluoroscopic X-ray table without the need for an overhead suspension system. The invention is used as part of a table capable of tilting up to 90° from horizontal in either direction along its longitudinal axis. The stability and rigidity is provided by eliminating the transverse carriage of the conventional X-ray table and allowing the spot film device to move transversely within the vertical carriage while the X-ray tube located in the table moves transversely within the longitudinal carriage. The longitudinal carriage thereby supports essentially only the weight of the X-ray tube and collimator assembly.

By being located in the longitudinal carriage, the X-ray tube is always positioned below the spot film device along the table's longitudinal axis. The vertical carriage does not move in the transverse direction thereby reducing the transversely moving mass. Rigidity is improved because one carriage supports the staging apparatus.

Another important feature of the invention is a variable length shaft, having means such as a pinion gear at one end and a means such as a sprocket at the other, which permits synchronous transverse movement of the spot film device and tube while retaining alignment between the two during vertical movement. The pinion gear means engages a rack means on the spot film device and the sprocket means drives means such as a roller chain and sprocket assembly which move so that the transverse movement of the spot film device induces transverse X-ray tube movement via the rotation of the shaft in the transverse direction.

A further aspect of the invention is the use of a cam associated with the shaft to permit different lengths of travel for the spot film device and the longitudinal carriage in the transverse direction. The spot film device may consequently be transversely moved beyond the range of the X-ray tube to be positioned out of the way of the table technician when not in use. This is accomplished by a cam preferably attached to the telescoping shaft. The rack, which engages and drives the pinion gear, has the same length as the range of movement of the X-ray tube carriage. When the gear reaches the end of the rack, a bar attached to the spot film device engages the cam, preventing the telescoping shaft from rotating while the spot film devices is allowed to travel further. The shaft and X-ray tube thereby remain locked in a park position at the end of their transverse range until the pinion reengages the rack. Other cam arrangements are possible and are described herein.

Another aspect of the invention is that the vertical carriage of the fluoroscopic staging apparatus is counterbalanced using a system of counterweights, pulleys, and cables. The cables are attached at one end to the counterweights and to the vertical carriage at the other end. As the vertical carriage carrying the spot film device moves up and down on its tracks in the staging apparatus, the counterweights move in the opposite direction and counterbalance the load. This counterbalance arrangement enables the vertical carriage to be raised and lowered by typically applying less than 8 pounds pressure to the handle on the spot film device.

Another aspect of the invention is that the entire fluoroscopic staging apparatus and spot film device are counterbalanced along the table's longitudinal axis such that when the table is tilted the spot film device can be moved in either direction with a minimum of force applied by the technician.

The counterbalance weights in both the longitudinal and vertical directions for the fluoroscopic staging and spot film device are contained in the same counterweight box. A power assist system is employed to move the staging and counterweights in either direction along the longitudinal axis of the table. A potentiometer located in the handle in the spot film device varies the polarity and magnitude of the power which activates a motor and magnetic clutch system. This drives a sprocket and chain arrangement attached to the longitudinal carriage which moves the fluoroscopic staging apparatus along the table's longitudinal axis.

Other objects, features and advantages of the invention will become apparent from the detailed description and drawings.

DETAILED DESCRIPTION OF THE INVENTION

Figure 1:
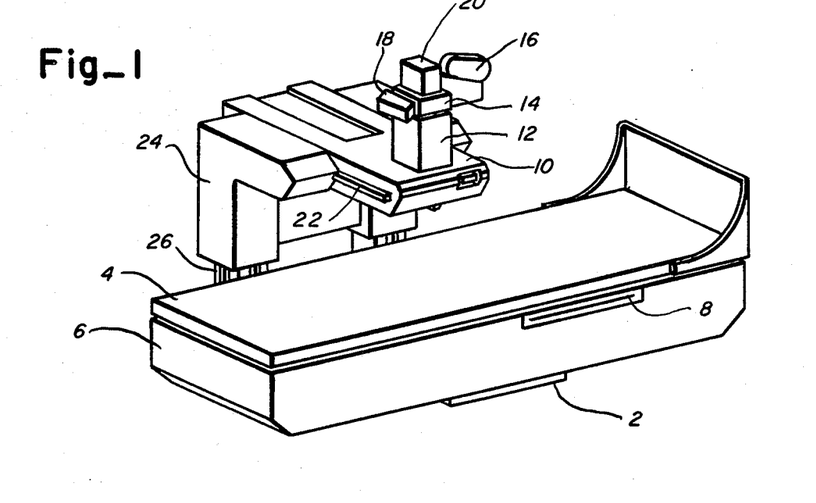
FIG. 1 shows a radiographic fluoroscopic X-ray table with a three port spot film system.

FIG. 1 shows a radiographic fluoroscopic X-ray table. The particular table shown is a 90/90 table; that is to say, it is capable of tilting the axis which runs the length of the table (hereinafter referred to as the longitudinal axis) ninety degrees in either direction with respect to the horizontal plane to which its base 2 is attached. In order to do this, the table's pivot axis is translated along its longitudinal axis simultaneously as the table rotates. Various apparatus and methods for translating and rotating 90/90 X-ray tables are old and well known.

The tabletop 4 is capable of being translated along the table's width and length relative to the table body 6. Various methods for moving the tabletop are also old and well known in the art. A is provided in the table body 6 to hold an X-ray film cassette for use with radiographic X-ray procedures which employ an overhead mounted X-ray tube to photograph the patient from above.

For performing fluoroscopic X-ray procedures, a spot film device 10 is mounted over the table surface 4. The particular spot film device shown employs a three port system with an image intensifier 12 and an optical distributor 14. Typically attached to the parts of the optical distributor are a 35 millimeter cine camera 16, a 105 millimeter spot film camera 18 capable of taking up to 12 frames per second, and a video camera 20 which may be connected to a monitor located elsewhere in the X-ray room. Naturally other photographic equipment used. Such three port systems are old and commonly used with fluoroscopic X-ray tables.

The spot film device 10 includes tracks 22 which are mounted for sliding movement against rollers within the vertical carriage 24 so that it may be moved transversely across the table top, i.e. in the direction of the table's width. The vertical carriage 24 in turn may be moved up and down along the tower 26 so that the distance between the spot film device 10 and the table surface 4 may be increased or decreased. The tower 26 is attached to a longitudinal carriage located within the table body 6. Movement of an X-ray tube attached to the longitudinal carriage is thereby synchronized with the movement of the spot film device coupled to the tower and is therefore always aligned with the image intensifier 12.

For convenience sake, FIG. 2 and FIG. 3, which respectively show the side and front of the vertical carriage, will be discussed together. The vertical carriage 24 slides along two pairs of tracks 28 and 30 affixed to the tower. The tracks 28 are affixed to the sides of the tower 26 pillars and the tracks 30 are attached to the front of the tower. Two sets of roller bearings 32, each set comprising two pairs of other bearings, are located on each side of the vertical carriage 24 to accept a respective one of the tracks 28 and 30 attached to the tower 26. It may be appreciated that as the spot film device 10 is raised and lowered with respect to the table top 4, the vertical carriage 24 travels vertically on the tracks 28 and 30.

The spot film device 10 moves transversely by means of three tracks 22 respectively to its bottom and sides and fitted for guided movement between respective sets of bearings 34 located in the vertical carriage.

Figure 2:
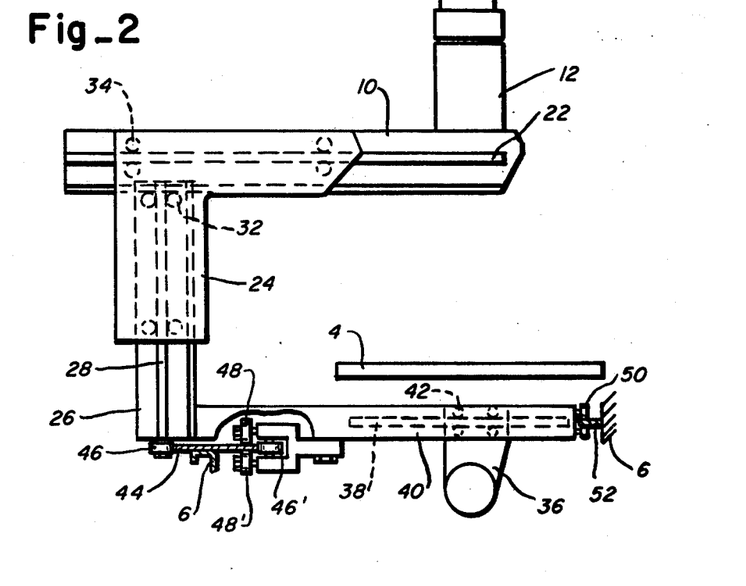
FIG. 2 is a side view of the fluoroscopic staging apparatus and spot film device.
Figure 3:
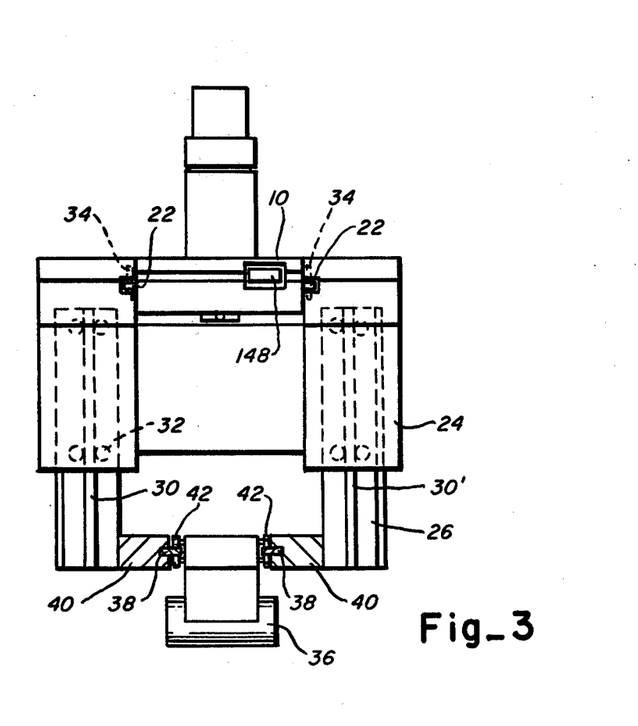
FIG. 3 is a front view of the fluoroscopic staging apparatus and spot film device.

As further shown in FIG. 2, the table houses a track 38 which is attached to a longitudinal carriage 40. An X-ray tube and collimator assembly 36 is mounted on the track 38 for guided movement by means of a longitudinal carriage 40. The assembly 36 is synchronized with the spot film device 10 so that the X-ray tube in the table remains directly beneath and aimed towards the aperture in the spot film device 10. FIG. 3 shows both sides of the longitudinal carriage 40 and the roller bearing sets 42 which slide along the two rails 38 that support the X-ray tube assembly 36.

The vertical carriage 24 together with the tower 26 and the longitudinal carriage 40 constitute the support assembly between the spot film device 10 and the X-ray table. This support assembly is called the fluoroscopic staging apparatus (hereinafter referred to as "staging"). As shown in FIG. 2 the staging is guided in the direction parallel to the longitudinal axis by a thick steel rail attached to the table housing 6 by means of cam follower bearings 46, 46', and 48, 48' respectively coupled to each side of the staging apparatus. The bearings 46, 46', and 48, 48' carry the principal load ride on the rail 44 parallel to the table's longitudinal axis.

Also shown in FIG. 2 is a roller bearing set 50 attached to the longitudinal carriage 40 on the opposite end from the bearing set 46 and 48. The bearing set 50 slides along a longitudinal rail 52 which is also attached to the table housing 6. Another bearing set 50 is attached to the end of the other beam of the longitudinal carriage 40 and also rides on rail 52. The bearings sets 50 and the rail 52 provide stability for the staging and prevent it from rotating about the table's longitudinal axis.

Figure 4:
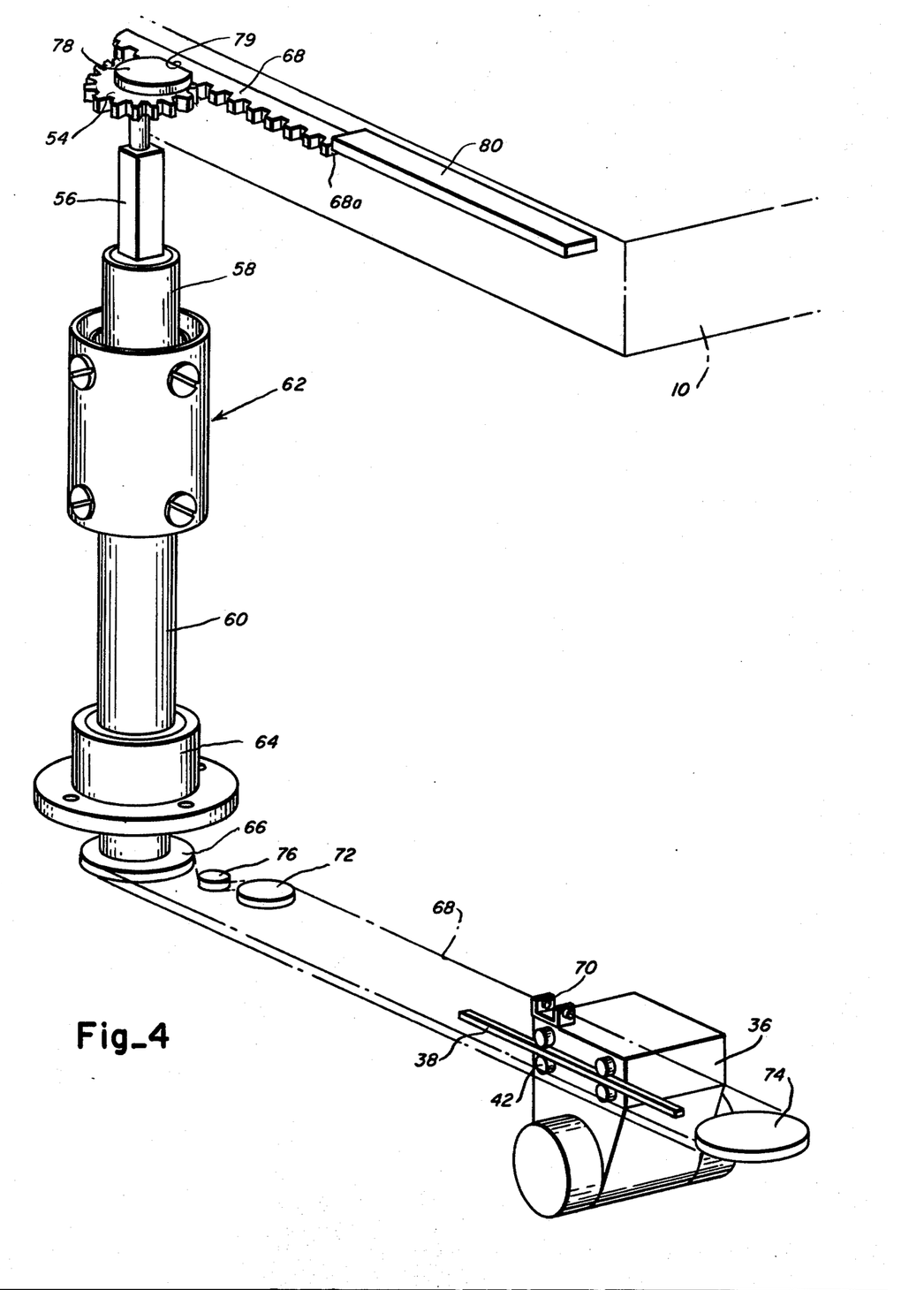
FIG. 4 shows the telescoping shaft assembly driven by a rack and pinion gear in the spot film device and connected to the X-ray tube carriage by way of a roller chain.
Figure 5:
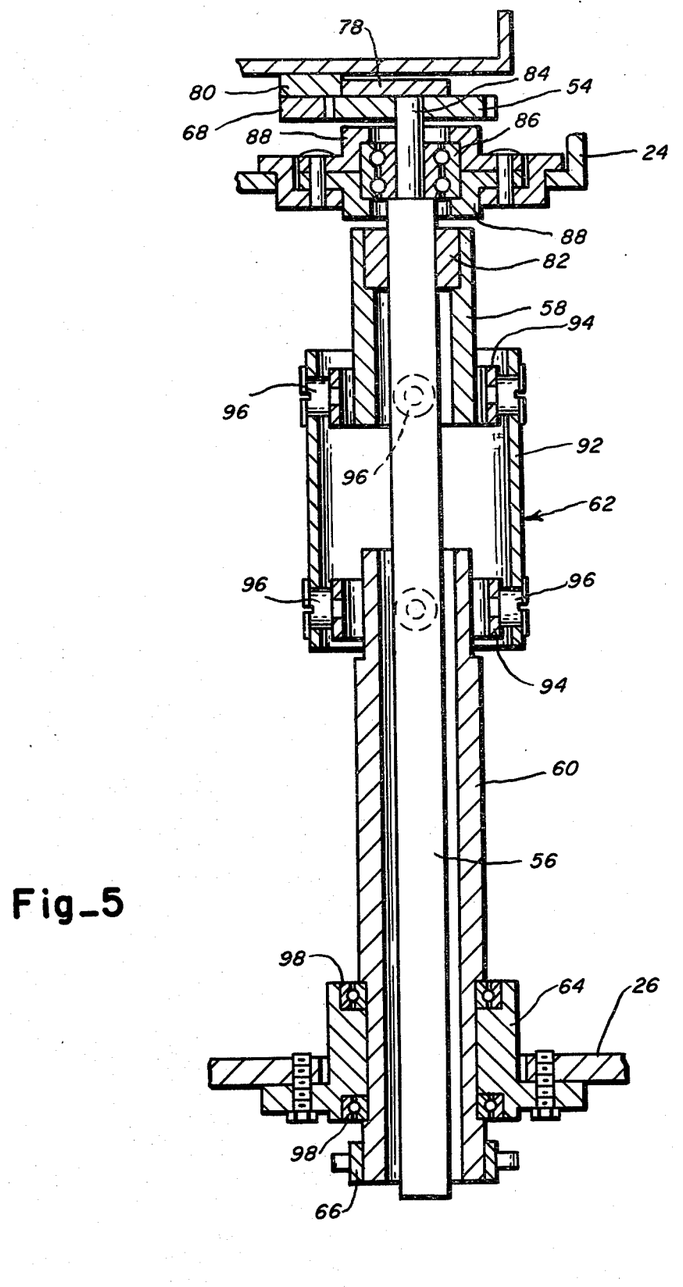
FIG. 5 shows a cut-away drawing of the telescoping shaft attached to the vertical carriage and tower and the cam engaging the spot film device.

FIG. 4 illustrates the means by which the X-ray tube and collimator assembly 36 lying below the table top 4 (FIG. 1) is maintained in alignment with the spot film device 10 contained in the vertical carriage 24 (FIG. 1). A square shaft 56 is coupled to the spot film device 10 via a pinion gear 54 and rack 68. An upper vertical tube 58 has a bore sized and shaped to accommodate the shaft 56 while restricting its rotation within the tube 58. A lower vertical tube 60 is connected to the upper tube 58 by way of a double universal joint 62. The resulting tube and universal joint assembly is mounted, at one end, in bearings, in a tube housing 64 affixed to the tower 26 (FIG. 1). The square 56, the tuges 58 and 60, and the double universal joint 62 form a telescoping shaft fixed at one end in the tower and movable at the other end with the vertical carriage. As the vertical carriage 24 (FIG. 1) containing the spot film device 10 is raised and lowered with respect to the tabletop 4 (FIG. 1), the shaft 56 slides in and out of the upper tube 58 so that the length of the shaft assembly increases and decreases while each segment of the shaft remains rotationally fixed with respect to the other shaft members. FIG. 5, which will be discussed later, shows a more detailed picture of the telescoping shaft.

As illustrated in FIG. 4, the end of lower tube 60 includes a chain sprocket 66 rigidly fixed thereto. The pitch diameter of the sprocket 66 is the same as the pitch diameter of pinion gear 54. As the spot film device 10 is moved along the transverse axis, the rack 68 attached to the spot film device drives the pinion gear 54 which rotates the shaft assembly and sprocket 66. A roller chain 68 is driven by the sprocket 66 and causes the X-ray tube and collimator 36 to travel along the transverse axis in the longitudinal carriage. The roller chain 68 is attached to the X-ray tube assembly by bracket 70. Sprockets 72 and 74 in the longitudinal carriage are used to maintain proper alignment of the roller chain 68. Sprocket 76 is also attached to the longitudinal carriage and takes up slack in the roller chain. Since the pitch diameter is the same for both the sprocket 66 and the pinion gear 54, as the pinion 54 is driven by the rack 68, the X-ray tube assembly 36 will travel the same distance as the spot film device 10.

The total range of movement for the X-ray tube and collimator assembly 36 along the table's transverse axis is less than the length of the rack 68. When the pinion gear 54 reaches the forward end of 58a of the rack 68, the surface 79 of a cam 78, attached to the pinion 54 for rotation therewith, engages a bar 80 fixedly attached to the spot film device 10. The bar 80 is positioned to engage only the cam 78 and not the pinion gear 54. When the cam 78 is so engaged, the surface 79 may slide along the bar 80, but the cam cannot rotate. The shaft assembly is thereby prevented from rotating when the X-ray and collimator assembly 36 reaches the end of its transverse range. This feature allows the spot film device 10 to have a greater range of movement than the X-ray and collimator assemlby assembly that it may be positioned out of the way of the technician when not in use and still be synchronized with the tube when in use.

FIG. 5 shows a sectional view drawing of the telescoping shaft assembly installed in the staging. The square shaft 56 slides in and out of the upper and lower vertical tubes 58 and 60 through a slide bushing 82 which is securely fastened to the upper vertical tube 58. The slide bushing is made of a commercially available bronze which is impregnated with oil to permit ease of movement of the square shaft 56 through the square hole in the bushing 82. The round upper end 84 of the square shaft 56 is pressed into a double row ball bearing 86. The outer race of the bearing 86 is secured to the vertical carriage 24 by means of clamps 88. As the vertical carriage moves up and down, the clamps 88 cause the square shaft 56 to move with it and vary the length of the telescoping shaft assembly. The drawing in FIG. 5 shows the cam 78 engaging the bar 80 on the spot film device so that the shaft assembly is locked into position and not free to rotate.

The double universal joint assembly 62 consists of a connector tube 92, two pivot rings 94, and eight pivot screws 96. Each pivot ring 94 is attached to the connector tube 92 by two pivot screws 96 arranged along an axis perpendicular to the plane of the paper as shown by dashed lines. Likewise, the lower pivot ring is attached to the lower vertical tube 60 by way of two pivot screws 96 arranged along an axis perpendicular to the plane of the paper. With the connector tube 58 and the lower vertical tube 60 to turn in unison substantially about their common axis while permitting relative movement in two dimensions, thereby preventing binding or stiffness between the slide bushing 82 and the square shaft 56 due to misalignment in the shaft assembly. A flexible boot, made of rubber or other material, may be used alternatively.

The lower vertical tube 60 is secured to the tower 26 by the tube support housing 64. The vertical tube 60 is fixedly secured along its axis but able to freely rotate through use of two ballbearing assemblies 98. FIG. 5 shows the sprocket 66 attached at the lower end of the vertical tube 60.

Figure 6:
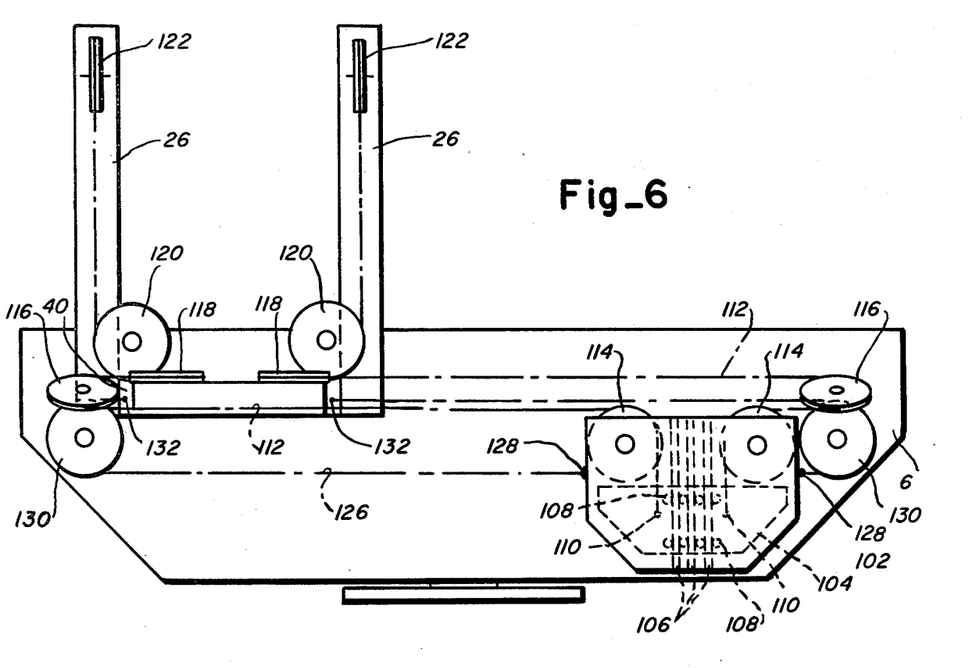
FIG. 6 shows the counterweight assembly used for counterbalancing the fluoroscopic staging apparatus in the X-ray table and the cables and pulleys used in the counterbalance system.

FIG. 6 shows the counterbalance mechanism for the fluoroscopic staging apparatus in the table. The weight box 102 which carries a vertical counterbalance weight 104 (shown by dashed lines) is mounted in the table housing 6. The vertical counterbalance weight 104 moves up and down in the box 102 along track 106 attached to the box 102 and roller bearings 108 attached to the weight 104. The weight 104 is counterbalanced against the vertical carriage 24 and spot film device 10 through a system of pulleys and cables.

Figure 7:
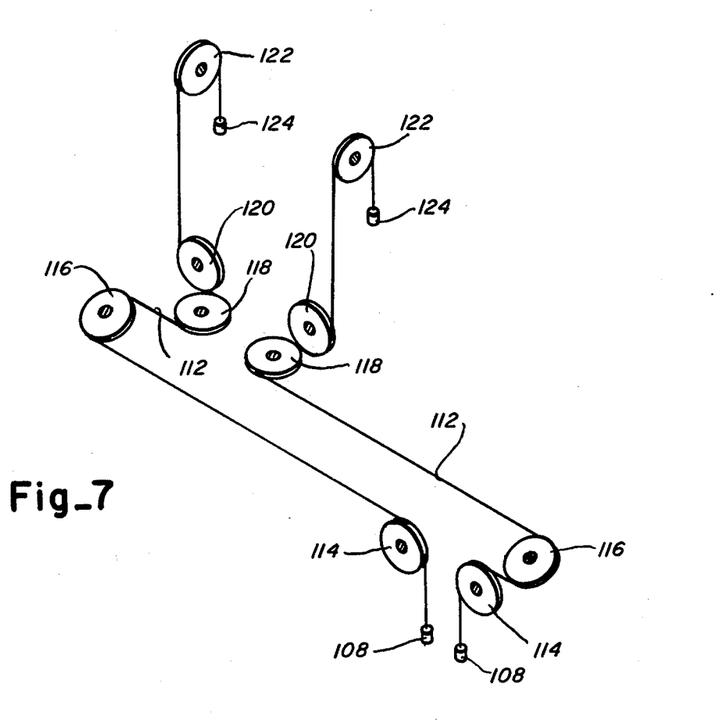
FIG. 7 is an isometric drawing showing the cables and pulleys used in the vertical counterbalance system for the vertical carriage.

Two cables 112 are attached to the counterweight at points 110. Aircraft cable is used which is attached with crimped ball fittings on the ends. The two vertical counterbalance cables 112 are carried over two pulleys 114 mounted on the weight box 102. The cable then passes to two pulleys 116 mounted at angles in either end of the table housing 6. The cables then are carried over two horizontal pulleys 118 attached to the longitudinal carriage 40 in the staging. Each pulley carries only one of the cables 112. Each of the cables is then guided to one of the pulleys 120 and then to the top of the tower 26 over pulleys 122. After the two cables 112 pass over the two pulleys 112 they are secured to the vertical carriage 24, not shown in FIG. 6. As the vertical carriage 24 moves up and down along its tracks in the tower 26, the vertical counterbalance weight 104 in the box 102 moves down and up in the opposite direction along its tracks 106. The mass of the spot film device and vertical carriage is approximately equivalent to the mass of the counterweight 104. FIG. 7 shows an isometric arrangement of the counterbalance cables 112 and the counterbalance pulley system. As shown the pulleys 114 are mounted in the box 102. Pulleys 116 are mounted in the table housing at angles from horizontal, pulleys 118 are mounted horizontally on the longitudinal carriage 40, and pulleys 120 and 122 are mounted vertically in the tower 26. Also note that while both pulleys are mounted vertically in the tower, they are mounted with their turn axis perpendicular to each other. The vertical carriage 24 is attached to the cables on one end at points 124 and the counterbalance weight is attached on the other ends at points 108.

Referring back to FIG. 6, the entire weight box 102 slides along the table's longitudinal axis on a track which will be discussed later with reference to FIG. 8. The box 102 travelling parallel to the longitudinal axis acts as a counterbalance for the staging and moves in the opposite direction that the staging moves. It is connected to the staging using two longitudinal counterbalance cables 126 which are secured to the box 104 at points 128. The two cables 126 pass over two pairs of pulleys 130 located at either end of the box's range of travel in the table housing 6 and attach to the staging at points 132.

Figure 8:
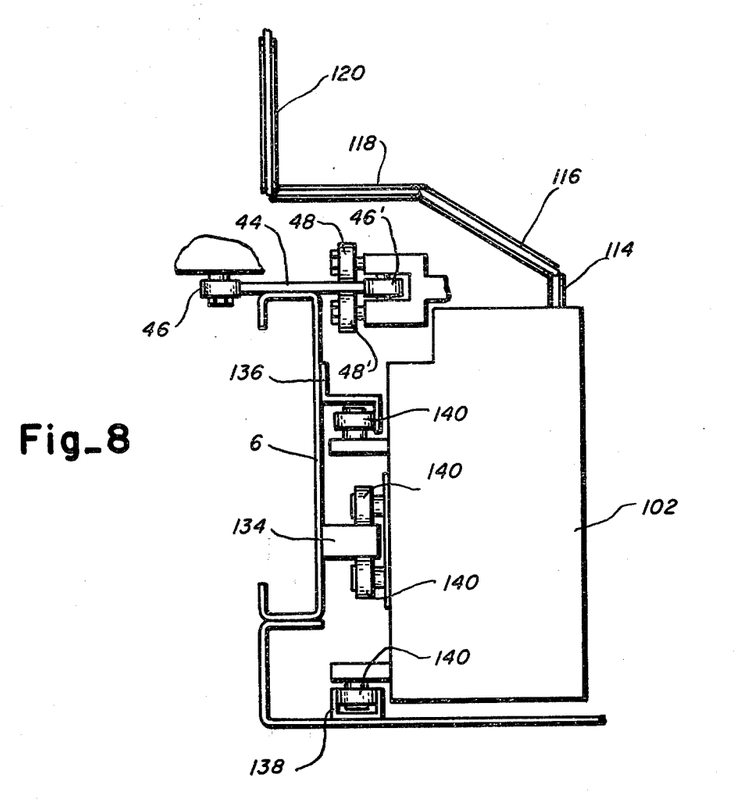
FIG. 8 shows the counterweight box installed in the table housing so that it can move along the table's longitudinal axis in the longitudinal counterbalance system.

The view of FIG. 8 is perpendicular to the longitudinal axis of the table and shows the box 102 supported for movement in and out of the plane of the drawing by a rail 134 attached to the table housing 6. The box 102 is secured against rotational movement by tracks 136 and 138 which are also attached to the table housing 6. Cam follower roller bearings 140 are employed to secure the box 102 to the rail 134 and tracks 136 and 138 so it can move freely along the table's longitudinal axis.

Also shown in FIG. 8 are roller bearings 46, 46', 48 and 48', which carry the staging along the rail 44. A portion of the vertical counterbalance system, described with respect to FIG. 6 is shown comprising pulley 114 contained inside the box 102, pulley 116 mounted to the table housing 6 and pulleys 120 and 118 which are secured to the staging.

Figure 9:
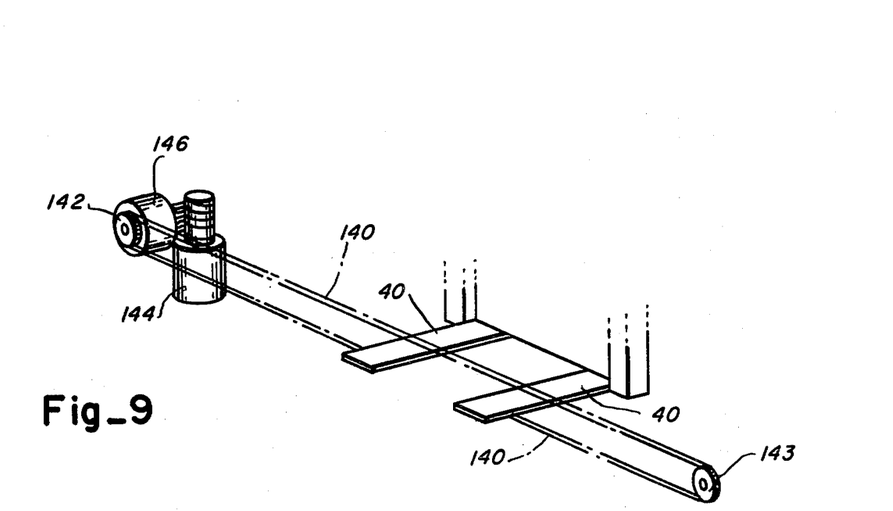
FIG. 9 shows the power-assist system which drives the fluoroscopic staging apparatus along the table's longitudinal axis.

FIG. 9 is a perspective view of the power-assist system for moving the staging along the table's longitudinal axis. A roller chain 140 is supported by two sprockets 142 and 143 located at either end of the table housing 6 and is attached to the longitudinal carriage 40. One sprocket 142 is driven by a shunt wound DC gear motor and drive assembly 144 and a magnetic particle clutch 146. The output shaft of the clutch 146 are connected using a common flexible coupling which attaches to both shafts by key ways and screws. Referring back briefly to FIG. 3, the motor 144 and clutch 146 are activated by a switch located in the handle 148 on the spot film device 10. By pushing either to the right or the left on the handle 148, the handle moves slightly with respect to the spot film device and varies the output of a potentiometer located inside of the handle.

Figure 10:
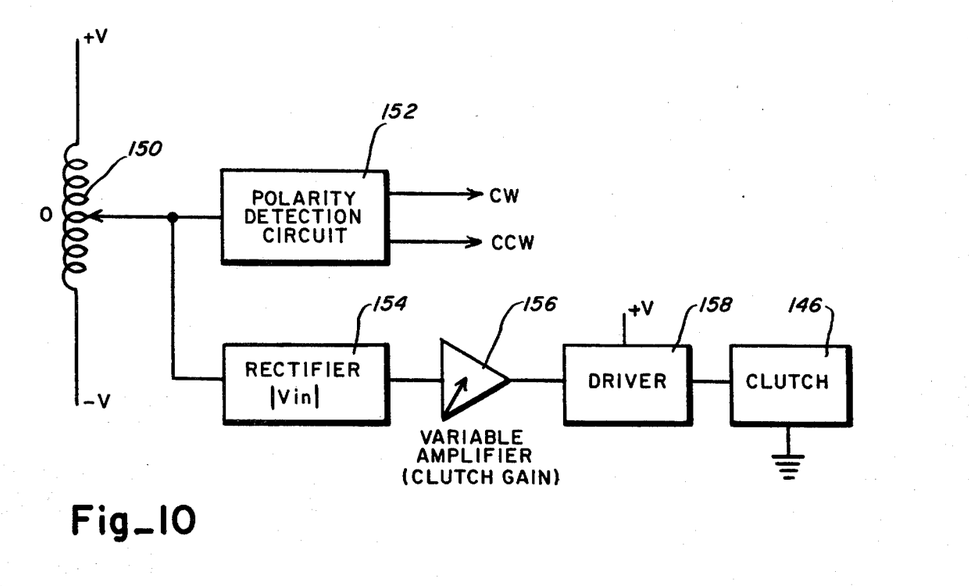
FIG. 10 is a schematic diagram of the circuitry used to activate the magnetic clutch and electric motor of the power-assist system.

FIG. 10 shows the circuitry which activates the motor 144 and the clutch 146. The potentiometer 150 located inside the handle is set at zero output when no longitudinal force is applied to the handle, the polarity of the potentiometer's output indicates the direction of movement desired. This output passes through a polarity detection circuit 152 which activates the motor 144 in either the clockwise or counterclockwise direction, depending on the polarity.

The magnitude of the potentiometer output indicates the magnitude of the force applied. This circuit output is also transferred to a rectifier circuit 154 whose output varies only in magnitude, but not polarity. This rectifier output passes through a variable amplifier 156 which is used to adjust the clutch gain and then to a driver circuit 158 which increases the current capacity of input to the clutch 146. Accordingly, the greater the force applied to the handle, the more torque applied by the clutch 146 to the sprocket 142.

Modifications to the embodiment described may be made without departing from the spirit of the present invention. For example, a table capable of rotating less than 90 degrees from horizontal or, a non-rotating table could be used, the power-assist drive system could be modified or eliminated. The counterbalancing could be changed or eliminated in whole or in part, or the cam 78 could be coupled to the rack 68 to push the pinion gear 54 away from the rack 68 when disengagement is required at the end of the collimator travel. Additionally, the rack and pinion could be replaced by means such as a chain and sprocket for translating linear motion to rotary movement. Accordingly, it will be understood that the invention is to be defined only by the following claims and is not intended to be limited by the foregoing description.

We claim:

1. In a radiographic system of the type typically including
   a table for supporting the radiographed subject,
   means for producing and directing radiographic beams to the area of the subject to be radiographed,
   beam receiving means for producing and displaying the radiographic image of the radiographed area,
   means for supporting the beam-directing means and beam-receiving means on opposite sides of the table,
   means for moving the beam-directing and beam-receiving means in alignment in generally transverse and longitudinal directions, and
   means for moving at least one of the beam-directing and beam-receiving means generally vertically while generally maintaining their alignment
   the improvement comprising:
   first carriage means mounted within the table body for generally longitudinal movement and adapted to support one of the beam-directing means and beam-receiving means as the lower beam means, the first carriage means including first guide means for permitting generally transverse movement of the lower beam means;
   a generally vertically extending support member coupled to the first carriage means for longitudinal movement therewith and extending outward from the table;
   second carriage means mounted for guided generally vertical movement and adapted to support a housing containing the other of the beam-directing and beam-receiving means in alignment with the lower beam means and including second guide means for permitting generally transverse movement of said housing and
   means for synchronizing the transverse movement of the beam-directing and beam-receiving means.

2. The system of claim 1 wherein the synchronizing means includes a variable length shaft,
   first means coupling one end portion of the shaft to the first guide means to cause lateral movement of said lower beam means in response to shaft rotation and means coupling a second end portion of the shaft to the second guide means to cause shaft rotation in response to the lateral movement of said housing.

3. The system of claim 2 wherein the second coupling means includes a gear-like driving member mounted generally perpendicular to the shaft axis for rotation therewith, and
   a generally transversely disposed plurality of gear-engaging surfaces mounted for movement with the housing to produce driving-member rotation with transverse housing movement.

4. The system of claim 3 wherein the driving member and engaging surfaces are a sprocket and chain respectively.

5. The system of claim 3 wherein the gear member and engaging surfaces are a pinion gear and rack, respectively.

6. The system of claim 2 wherein the first coupling means includes a sprocket member mounted on the shaft perpendicular to the shaft axis for rotation therewith and
   a chain having sprocket-engaging links and coupled at its ends to transversely displaced locations on said lower beam means, whereby rotating gear movement produces transverse movement of the lower beam means in accordance with said first guide means.

7. The fluoroscopic X-ray table described in claim 2 wherein said shaft includes
   a first shaft segment having a first cross-section,
   a second shaft segment having an axially extending cavity, the cavity cross-section being larger than said first cross-section, whereby said first segment telescopes into said second segment,
   means for constraining the rotational movement of said first segment within said second segment while permitting translational movement between said segments along the axis of rotation.

8. The fluoroscopic X-ray apparatus described in claim 7 wherein said first shaft segment includes a non-circular segment and said constraining means includes a bushing affixed to said second segment with a hole slightly larger than the size and shape of said noncircular segment cross-section to receive said first segment so that said first segment fits inside of said second segment along the axis of rotation of said shaft and said bushing constrains the two segments to rotate in unison about the axis while permitting translational movement between the two segments along the axis.

9. The system of claim 2 including
   a gear-like driving member mounted generally perpendicular to the shaft axis for rotation therewith,
   a generally transversely disposed plurality of nonslipping, driving member engaging surfaces mounted for movement with said housing for producing shaft rotation in response to lateral movement of said housing, and
   means for preventing shaft rotation for transverse movement of the housing beyond a predetermined transverse position, while permitting further transverse movement of said housing, whereby said housing and said lower beam means have different ranges to transverse movement and the beam-receiving and beam-producing means are maintained in alignment only within the common range.

10. The system of claim 9 including
    a longitudinally-extending surface member coupled to the housing for transverse movement therewith,
    a generally complimentary surface member associated with the shaft, and shaped to permit transverse sliding contact of the surfaces,
    the surface members being relatively positioned to contact each other when said housing is outside the common travel range and to disengage the driving member from the engaging surfaces during contact.

11. The system of claim 9 including
a longitudinally-extending surface member coupled to said housing for transverse movement therewith;
a rotating member associated with the shaft and having a surface oriented to engage the surface member for sliding contact when said housing is transversely moved outside the common range to prevent rotation of the rotating member.

12. The system of claim 2 wherein the shaft includes first and second segments in a generally opposing end-to-end relationship,
coupling means for permitting parallel and angular misalignment between the segments.

13. The system of claim 12 wherein the coupling means includes a firm but resilient sleeve encompassing the opposing ends.

14. The system of claim 12 wherein the coupling means includes a double universal joint arranged to permit two dimensional misalignment between the respective segment axes.

* * * * *